US00PP08797P

United States Patent [19]

VandenBerg

[11] Patent Number: Plant 8,797

[45] Date of Patent: Jun. 21, 1994

[54] CHRYSANTHEMUM PLANT NAMED CORAL CORRIDA

[75] Inventor: Cornelis P. VandenBerg, Salinas, Calif.

[73] Assignee: Yoder Brothers, Inc., Barberton, Ohio

[21] Appl. No.: 35,960

[22] Filed: Mar. 23, 1993

[51] Int. Cl.[5] ..... A01H 5/00

[52] U.S. Cl. ..... Plt./82.3

[58] Field of Search ..... Plt. 74.1, 82.3

[56] References Cited

U.S. PATENT DOCUMENTS

PP 8,180 3/1993 VandenBerg ..... Plt./82.4

4,616,099 10/1986 Sparkes ..... 47/58 X

OTHER PUBLICATIONS

Dowrick, G. J., et al., (1966) "The induction of mutations in Chrysanthemums with X and Gamma Rays", *Euphytica* 15: 204–210.

Machin, B. J., "Sporting and Irradiation" *The Chrysanthemum Manual,* 1979, The National Chrysanthemum Society, London, pp. 329–336.

Broertjes, C., et al., "Chrysanthemums", *Application of Mutation Breeding Methods in the Improvement of Vegetatively Propagated Crops,* 1978, Elsevier, Sci. Pub. Co. N.Y., pp. 162–175.

Chan, A. P., (1966) "Chrysanthemum and Rose Mutations Induced by X Rays" Proceedings Amer. Soc. Hort. Sci. 88: 613–620.

Broertjes, C., (1966) "Mutation Breeding of Chrysanthemums" Euphytica 15:156–162.

Broertjes, C., et al., (1980) "A Mutant of a Mutant of a Mutant of a . . . Irradiation of Progressive Radiation-Induced Mutants in a Mutation-Breeding Programme with *Chrysanthemum morifolium*" Euphytica 29:525–530.

Searle, S. A., et al., "Use of Gamma and X Rays", *Chrysanthemums the Year Round,* 1958, Blandford Press, Ltd., London, pp. 27–29.

Sigurbjornsson, B., "Chapter 8 Induced Mutations", *Crop Breeding,* 1987, American Society of Agronomy and Crop Science Society of America, pp. 153–176.

*Primary Examiner*—James R. Feyrer

*Attorney, Agent, or Firm*—Foley & Lardner

[57] ABSTRACT

A Chrysanthemum plant named Coral Corrida particularly characterized by its flat capitulum form; spooned anemone capitulum type; coral ray floret color; diameter across face of capitulum of 76 to 83 mm when fully opened, when grown as a single stem cut mum; photoperiodic flowering response to short days when grown in Salinas, Calif., is 49 to 54 days after start of short days. Flowering response in Bogota, Colombia is 68 to 71 days; plant height is 81 to 99 cm when grown in Salinas with 11 to 18 long days prior to start of short days; height is 114 cm when grown in Bogota with 21 long days prior to start of short days; peduncle length of the first lateral at flowering after removing the apical bud without growth regulator applications is 5 to 10 cm when grown in Salinas, and 8 cm when grown in Bogota. Peduncle length of the fourth lateral at flowering is 8 to 13 cm when grown in Salinas, and 10 to 13 cm when grown in Bogota; and excellent tolerance to low night temperatures for bud initiation and flower development.

1 Drawing Sheet

The present invention comprises a new and distinct cultivar of Chrysanthemum, botanically known as *Dendranthema grandiflora,* and referred to by the cultivar name Coral Corrida.

Coral Corrida, identified as 1090 (86-910A01), is a product of a mutation induction program. The new cultivar was discovered and selected by Cornelis P. VandenBerg on Nov. 28, 1990, in a controlled environment in Salinas, Calif., as one flowering plant within a flowering block established as rooted cuttings from stock plants which had been exposed as unrooted cuttings to an X-ray source of 1500 rads in Fort Myers, Fla., on Jun. 28, 1990. Reselection was done on Jul. 16, 1991 by Cornelis P. VandenBerg after flowering of the original selection exhibited a mixture of stems with light purple flowers and stems with coral flowers.

The irradiated parent cultivar was the cultivar identified as Corrida, disclosed in my Plant patent application Ser. No. 07/745,700 now U.S. Plant Pat. No. 8,180. Corrida can be described as a spray cut mum with a flat capitulum form; spooned anemone capitulum type; light purple ray floret color; diameter across face of capitulum of 76 to 83 mm when fully opened; flowering response period of 48 to 55 days after start of short days in Salinas, Calif., and of 64 to 70 days in Bogota, Colombia; plant height of 69 to 91 cm when grown in Salinas with 14 to 18 long days prior to start of short days, and 102 to 117 cm when grown in Bogota with 21 long days prior to start of short days; and excellent tolerance to low night temperatures for bud initiation and flower development. The foregoing description of Corrida has a somewhat wider range of measurements than the description of Corrida in the pending application noted. This is based on the continued flowering trials of Corrida after preparing and filing the application for Corrida.

The irradiation program resulting in Coral Corrida had as its primary objective the expansion of color ranges of the parent cultivar Corrida. The irradiation program comprised irradiating cuttings of the parent cultivar at irradiation levels of 1500, 1750 and 2000 rads. A total of 706 cuttings harvested from a total of 225 irradiated plants were planted on Sep. 24, 1990, Sep. 17, 1990 and Sep. 17, 1990, respectively. Of these, 6 initial selections were made, which selections were then revegetated and reflowered. Three consecutive flowerings resulted in discarding 2 of the original 6 selections on Aug. 9, 1991, while 3 codes were retained as PI (Possible Introduction) status. One code was reselected under code number 1090 on Jul. 16, 1991 and also given PI status. The original selection which was reselected (code 3556) was discarded from the program on Aug. 9, 1991. The three retained codes and the reselected code were further tested in Salinas, Calif., and in Bogota, Colombia, ultimately resulting in discarding two of these codes, and the decision to introduce the reselected code 1090 as Coral Corrida and code 3555 as White Corrida. The latter is disclosed in a pending application.

The first act of asexual reproduction of Coral Corrida was accomplished when vegetative cuttings were taken from the reselected selection in September 1991 in a controlled environment in Salinas, Calif., by technicians working under supervision of Cornelis P. VandenBerg.

Horitcultural examination of controlled flowerings of successive plantings has shown that the unique combination of characteristics as herein disclosed for Coral Corrida are firmly fixed and are retained through successive generations of asexual reproduction.

Coral Corrida has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and in Bogota, Colombia, under greenhouse conditions which approximate those generally used in commercial greenhouse practice. The low night temperature tolerance was determined in repeated flowerings in Bogota, Colombia at temperatures as low as 5-10 degrees Celsius.

The following traits have been repeatedly observed and are determined to be basic characteristics of Coral Corrida, which, in combination, distinguish this Chrysanthemum as a new and distinct cultivar:

1. Flat capitulum form.
2. Spooned anemone capitulum type.
3. Coral ray floret color.
4. Daimeter across face of capitulum of 76 to 83 mm when fully opened, when grown as a single stem spray cut mum.
5. Photoperiodic flowering response to short days when grown in Salinas, Calif., is 49 to 54 days after start of short days. Flowering response in Bogota, Colombia is 68 to 71 days.
6. Plant height is 81 to 99 cm when grown in Salinas with 11 to 18 long days prior to start of short days; height is 114 cm when grown in Bogota with 21 long days prior to start of short days.
7. Peduncle length of the first lateral at flowering after removing the apical bud without growth regulator applications is 5 to 10 cm when grown in Salinas, and 8 cm when grown in Bogota. Peduncle length of the fourth lateral at flowering is 8 to 13 cm when grown in Salinas, and 10 to 13 cm when grown in Bogota.
8. Excellent tolerance to low night temperatures for bud initiation and flower development.

The accompanying photographic drawing is a side view of a single stem cut spray mum of Coral Corrida, with the colors being as nearly true as possible with illustrations of this type.

Of the commercial cultivars known to the inventor, the most similar in comparison to Coral Corrida is the parent cultivar Corrida. All traits of Coral Corrida are similar to those of Corrida, except for the ray floret color, the flowering response, and the plant height. Coral Corrida has a slower flowering response to short days, ranging between one and three days, and a taller plant height of 3 to 10 cm when compared with Corrida.

In the following description color references are made to The Royal Horticultural Society Colour Chart. The color values were determined on plant material grown as a single stem spray cut mum in Salinas, Calif. on Dec. 15, 1992.

Classification:

*Botanical.*—*Dendranthema grandiflora* cv Coral Corrida.

*Commecial.*—Flat spooned anemone cut spray mum.

INFLORESCENCE

A. Capitulum:

*Form.*—Flat.

*Type.*—Spooned anemone.

*Diameter across face.*—76 to 83 mm when fully opened.

B. Corolla of ray florets:

*Color (general tonality from a distance of three meters).*—Coral.

*Color (upper surface).*—27A to 29C.

*Color (under surface).*—19C to 29D.

*Shape.*—Base tubular, apex flattened with spoon-like, with varying spoon length.

C. Corolla of disc florets (anemone cushion):

*Color (mature).*—12B.

*Color (immature).*—150A to 150B.

D. Reproductive organs:

*Androecium.*—Present on disc florets only; scant pollen.

*Gynoecium.*—Present on both ray and disc florets.

PLANT

A. General appearance:

*Height.*—81 to 99 cm when grown in Salinas with 11 to 18 long days prior to start of short days; height is 114 cm when grown in Bogota with 21 long days prior to start of short days.

B. Foliage:

*Color (upper surface).*—147A.

*Color (under surface).*—147B.

I claim:

1. A new and distinct Chrysanthemum plant named Coral Corrida, as described and illustrated.

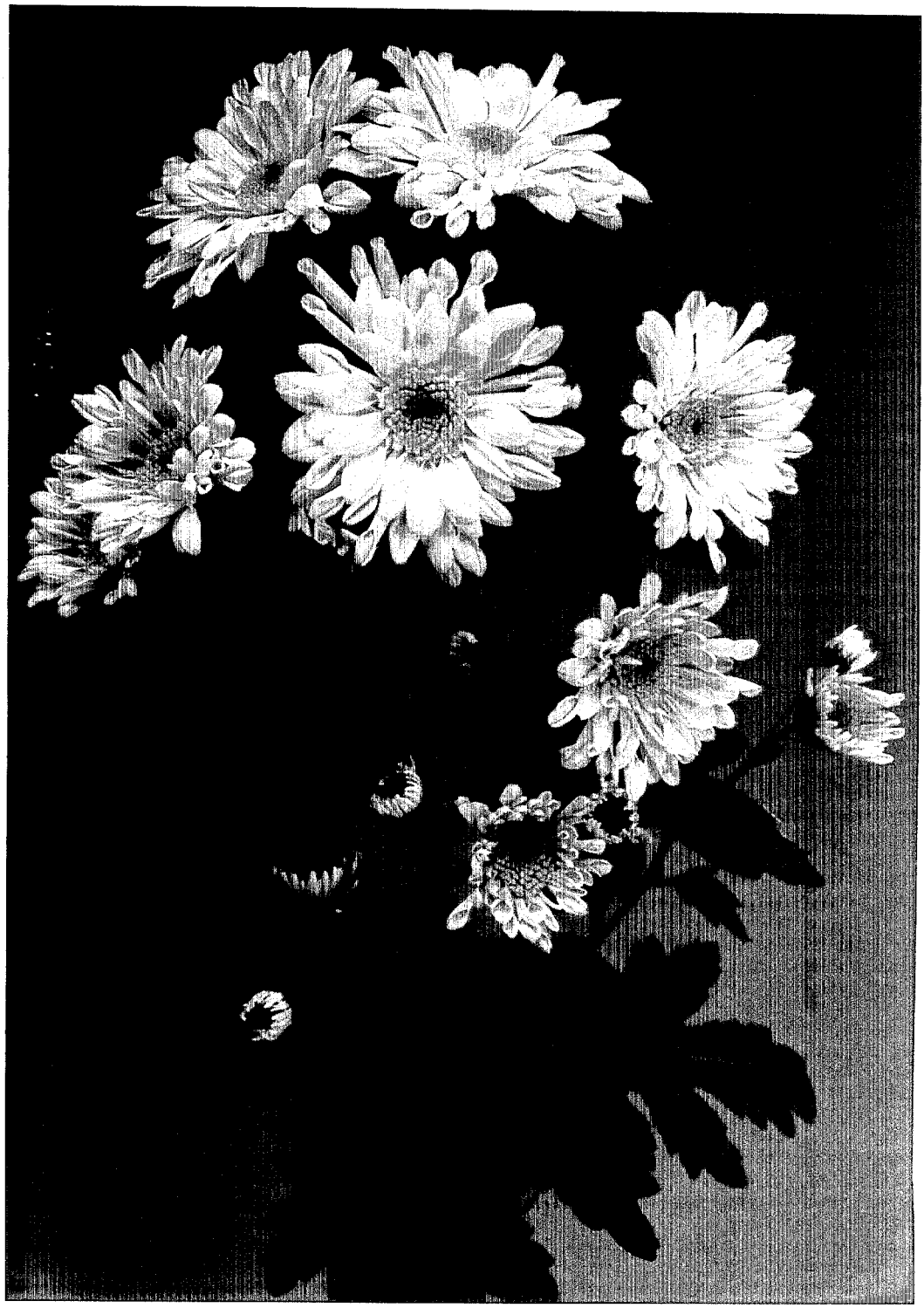

* * * * *